US00PP12218P2

(12) United States Plant Patent
Stemkens

(10) Patent No.: US PP12,218 P2
(45) Date of Patent: Nov. 20, 2001

(54) VERBENA PLANT NAMED 'SALMENA'

(75) Inventor: Henricus G. W. Stemkens, Hoorn (NL)

(73) Assignee: Syngenta Seeds B.V., Enkhuisen (NL)

( * ) Notice: Subject to any disclaimer, the term of this patent is extended or adjusted under 35 U.S.C. 154(b) by 0 days.

(21) Appl. No.: 09/614,737

(22) Filed: Jul. 13, 2000

(51) Int. Cl.[7] ..... A01H 5/00
(52) U.S. Cl. ..... Plt./308
(58) Field of Search ..... Plt./308

(56) References Cited

PUBLICATIONS

UPOV–ROM GTITM Computer Database 2001/01, Feb. 6, 2001, Gti Jouve Retrieval Software, Citation for Verbena 'Salmena'.*

* cited by examiner

*Primary Examiner*—Bruce R. Campell
*Assistant Examiner*—June Hwu
(74) *Attorney, Agent, or Firm*—Bruce Vrana

(57) ABSTRACT

A new Verbena plant particularly distinguished by its very large rose pink flower, early flowering, no seed set and hanging habit.

1 Drawing Sheet

BACKGROUND OF THE NEW PLANT

The present invention comprises a new distinct cultivar of Verbena, botanically known as *Verbena×hyrida*. The new cultivar is propagated from cuttings resulting from the cross of 'U1029' and 'U1030'. 'U1029' is a pink flowering Verbena having a semi-erect habit. 'U1029' is not commercially available and is not known by any synonyms. 'U1030' is a pink flowering Verbena having a spreading habit. 'U1030' is not commercially available and is not known by any synonyms. Neither 'U1029' or 'U1030' has been patented. As a result of this cross the present cultivar was created in 1996 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

DESCRIPTION OF THE DRAWING

This new Verbena plant is illustrated by the accompanying photographic drawings which show blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on 14 weeks old plants, blossomed under natural light in a greenhouse. Color readings were taken in the greenhouse under ambient light. Color references are primarily to the R.H.S. Colour Chart of The Royal Horticultural Society of London.

The Plant

Classification — Botanical: *Verbena×hybrida.*
Parentage:

*Female parent.*—A seedling named 'U1029' is one of our seedlings from our U-generation of plants bred in 1991.

*Pollen parent.*—A seedling named 'U1030' is one of our seedlings from our U-generation of plants bred in 1991.

Growth habit: Spreading and hanging.
Plant height: 10–20 cm.
Spreading area of plant: 80–120 cm.
Growth rate: Vigorous.
Strength: Good.
Branching character: Freely branching and lateral branching at every node.
Blooming period: From April until November.

The Stem

Diameter: 1.5–2 mm.
Shape: Tetragonal.
Color: Light green 141C.
Anthocyan pigmentation: Absent.
Length of internode: 15–75 mm, depending on the light where the plant is propagated.
Pubescence: Slightly pubescent.

The Foliage

Phyllotaxis: Opposite.
Points of attachment: Petiolate.
Shape of blade: Broadly ovate.
Texture:
*Upper side.*—Slightly pubescent.
*Lower side.*—Slightly pubescent.
Venation: Pinnate.
Leaf margin: Biserrate and irregularly incised.
Leaf apice: Acute.
Length: 20–30 mm.
Width: 25–30 mm.
Depth of incision: 2–3 mm.
Color:
*Upper side.*—Dark green 137A.
*Lower side.*—Light green 138A.
Length of petiole: 5–15 mm.
Color of petiole: Light green 141C.
Petiole surface texture: Slightly pubescent.

The Bud

Peduncle length: 30–65 mm, depending on season.
Size:
*Diameter.*—2 mm.
*Length.*—8–10 mm.
Shape: Elongated and ovate.
Color: Medium green 141B.
Color when calyx begins to unfold: Rose 52A.
Sepals:
*Color.*—Light green 138A.
*Form.*—Upright.
*Number.*—5, fused.
*Size.*—8 mm.
*Shape.*—Elongated.

The Flower

Direction: Ascending.
Diameter: 17–22 mm.
Corolla tube length: 16–18 mm.
Borne: In a cluster.
Form: Salverform; sessile on terminal spikes.
Cluster: Spike.
Color:
*Upper bloom surface.*—When opening rose 52B, after 4–6 days pink 54D.
*Lower bloom surface.*—Pink 54D.
Eye: A very small (1 mm) green-white eye (155D) is present. The three lower petals exhibit this green-white coloration at their bases.
No. of petals: Gamopetalous, five lobed.
Overlapping of petals: Separate.
Size of the petal:
*Length.*—6–8 mm.
*Width.*—5–7 mm.
Petal surface texture: Smooth.
Petal shape:
*Apex.*—Heart shaped (cordate).
*Base.*—Gamopetalous, so grown together.
Petal margin: Entire.
Spike:
*Length.*—30–60 mm.
*Diameter.*—35–60 mm.
Calyx: Length of 10–12 mm.
Anthocyan pigmentation of calyx limb: Absent.
No. of flowers per spike: 25–40.
Fragrance: A very soft rosy sweet fragrance is present.
Lastingness of individual blooms: New florets continue to open in one spike over an approximate 2 week period.

Reproductive organs

One pistil and four stamens in pairs; color for both is yellow green 150C. The pistil size is 16–18 mm in length. Pollen is not present. The filaments and anthers are fused to the corolla. The anthers are enclosed and not a prominent feature of the flower. 'Salmena' doesn't set seed at all.

Roots

Type of roots: Fibrous. Roots start to grow on every part of the stem that contacts the soil, so not only at the nodes.
Physiological and ecological characteristics: Good tolerance to heat and cold. Strong resistance to pests and diseases, particularly powdery mildew.

What is claimed is:

1. A new and distinct variety of Verbena plant, substantially as herein illustrated and described, characterized particularly as to novelty by larger rose pink flowers than other Verbena plants, which appear earlier on the plant, flowers that produce no seed and a growing habit that is spreading and very vigorous.

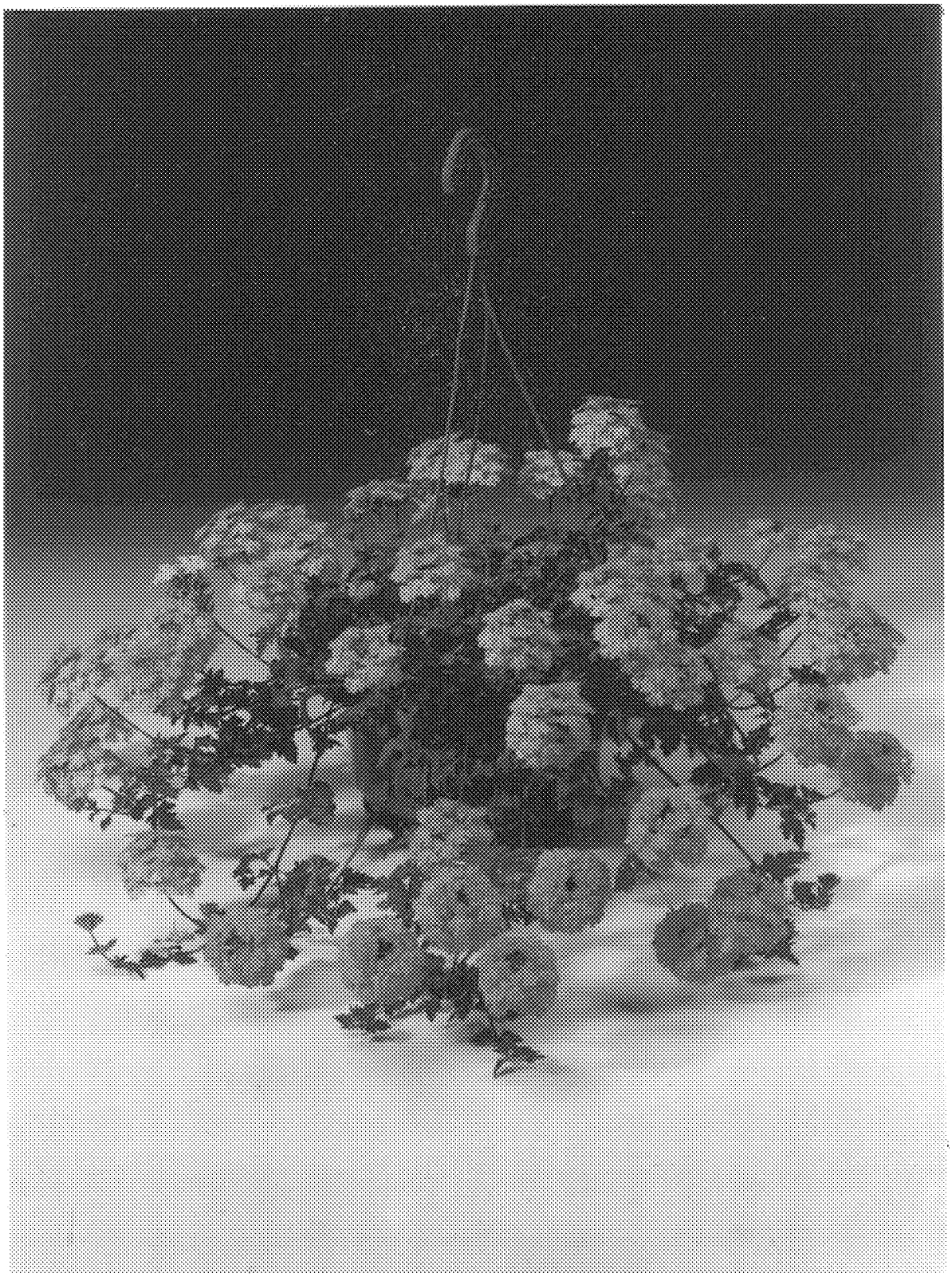

* * * * *